United States Patent [19]

Cavazza

[11] Patent Number: 5,861,434
[45] Date of Patent: *Jan. 19, 1999

[54] COMPOSITIONS CONTAINING L-CARNITINE OR AN ACYL L-CARNITINE IN COMBINATION WITH AN ACE-INHIBITOR FOR THE TREATMENT OF CARDIOVASCULAR DISORDERS AND A METHOD FOR TREATING CARDIOVASCULAR DISORDERS

[75] Inventor: Claudio Cavazza, Rome, Italy

[73] Assignee: Sigma-Tau Industrie Farmaceutiche Riunite S.p.A., Rome, Italy

[*] Notice: This patent issued on a continued prosecution application filed under 37 CFR 1.53(d), and is subject to the twenty year patent term provisions of 35 U.S.C. 154(a)(2).

[21] Appl. No.: 612,671

[22] Filed: Mar. 8, 1996

Related U.S. Application Data

[63] Continuation of Ser. No. 350,188, Nov. 30, 1994, abandoned, which is a continuation of Ser. No. 197,453, Feb. 16, 1994, abandoned, which is a continuation of Ser. No. 37,359, Mar. 26, 1993, abandoned.

[51] Int. Cl.⁶ .......................... A61K 37/12; A61K 37/44
[52] U.S. Cl. .......................... 514/561; 514/213; 514/221; 514/323; 514/409; 514/419; 514/423; 514/569
[58] Field of Search ...................... 514/561, 423, 514/412, 323, 419, 409, 213, 221, 569

[56] References Cited

U.S. PATENT DOCUMENTS

| | | | |
|---|---|---|---|
| 4,194,006 | 3/1980 | Cavazza | 424/311 |
| 4,599,232 | 7/1986 | Bertelli | 514/556 |
| 5,025,001 | 6/1991 | Loscalzo et al. | 514/91 |
| 5,037,851 | 8/1991 | Cavazza . | |
| 5,043,355 | 8/1991 | Cavazza . | |
| 5,145,871 | 9/1992 | Cavazza . | |
| 5,173,508 | 12/1992 | Cavazza . | |
| 5,192,805 | 3/1993 | Cavazza . | |
| 5,227,518 | 7/1993 | Cavazza . | |
| 5,270,472 | 12/1993 | Taglialatela et al. . | |
| 5,432,199 | 7/1995 | Cavazza . | |

*Primary Examiner*—Keith D. MacMillan
*Attorney, Agent, or Firm*—Oblon, Spivak, McClelland, Maier & Neustadt, P.C.

[57] ABSTRACT

Compositions containing (a) L-carnitine, an acyl L-carnitine, or a pharmacologically acceptable salt thereof in combination with (b) an ACE-inhibitor are useful for treating cardiovascular disorders. Orally, parenterally, rectally or transdermally administrable pharmaceutical compositions in unit dosage form contain from about 0.5 to about 2 g of L-carnitine, or an equimolar amount of an acyl L-carnitine or a pharmacologically acceptable salt thereof, and, e.g., from about 5 to about 20 mg of the ACE-inhibitor lisinopril.

17 Claims, No Drawings

COMPOSITIONS CONTAINING L-CARNITINE OR AN ACYL L-CARNITINE IN COMBINATION WITH AN ACE-INHIBITOR FOR THE TREATMENT OF CARDIOVASCULAR DISORDERS AND A METHOD FOR TREATING CARDIOVASCULAR DISORDERS

This application is a Continuation of application Ser. No. 08/350,188, filed on Nov. 30, 1994, now abandoned, which is a Continuation of application Ser. No. 08/197,453, filed on Feb. 16, 1994, abandoned, which is a Continuation of application Ser. No. 08/037,359, filed on Mar. 26, 1993, abandoned.

BACKGROUND OF THE INVENTION

1. Field of the Invention

The present invention relates to a method for treating cardiovascular disorders by administering L-carnitine, an acyl L-carnitine, or a pharmacologically acceptable salt thereof in combination with an ACE-inhibitor. The present invention also relates to orally, parenterally, rectally, or transdermally administrable pharmaceutical compositions suitable for treating cardiovascular disorders, which comprise, as active ingredients, L-carnitine, an acyl L-carnitine, or a pharmacologically acceptable salt thereof and an ACE-inhibitor.

2. Discussion of the Background

Previous therapeutical uses of L-carnitine are already known. For instance, L-carnitine has been used in the cardiovascular field in the treatment of acute and chronic myocardial ischemia, angina pectoris, cardiac arrhythmias and cardiac insufficiency. In nephrology, L-carnitine has been administered to chronic uremic patients who are subjected to regular hemodialysis treatment with a view to counteracting muscular asthenia and the onset of muscular cramps. Further therapeutic uses are the restoration of the HDL/LDL+VLDL ratio to normal and in total parenteral nutrition. The use of L-carnitine for the treatment of certain myopathies and muscular dystrophies is also known.

The ACE-inhibitors form a class of medicaments that has been recently introduced and are capable of preventing the conversion of angiotensin I into angiotensin II, with a consequent anti-hypertensive effect.

Typical ACE-inhibitors include: captopril, enalapril, lisinopril, ramipril, fosinopril, zofenopril, pivopril, rentiapril, quinapril, indolapril, spirapril, pentopril, benazepril, libenzapril, cilazapril, delapril and perindopril.

The main indications for which ACE-inhibitors are used are essential hypertension and renovascular hypertension.

Recently, combination preparations of ACE-inhibitors with various types of other medicaments have been proposed for the treatment of diverse pathological conditions. Examples of such combination preparations and the relative therapeutic indications are set out in Table 1.

TABLE 1

Known combination preparations of ACE-inhibitors with other medicaments

| Medicaments | Indications | Reference |
|---|---|---|
| Captopril + diltiazem | hypertension | US 4,871,731 |
| ACE-inhibitors + calcium antagonists | loss of cognitive functions, Alzheimer, senile dementia | EP 0 344 995 |
| ACE-inhibitors + thrombolitics | myocardiac post-ischaemia disfunction | EP 0 366 033 |
| ACE-inhibitor + lithium | depression | US 4,912,096 |
| ACE-inhibitors + calcium antagonists | medicament addiction | EP 381 075 |
| ACE-inhibitors + calcium antagonists | appetite suppression | EP 381 074 |
| ACE-inhibitor + flosequinam | cardiopathies myocardiac infarction | WO 90/10445 |

The combinations set out above, particularly if used in the cardiovascular field, do not appear to be wholly satisfactory in that it is foreseeable that the improved therapeutic activity would be accompanied by at least the sum of the side effects of the ACE-inhibitors themselves on the one hand and on the other hand the side effects of the medicaments combined with them.

In particular, in the case of the compositions containing calcium antagonists, side effects caused by excessive peripheral vasodilatation with consequent tachycardial reflex effects are to be expected.

With regard to the use of acyl carnitines in combination with other medicaments, U.S. Pat. No. 4,537,772 discloses combinations of acyl carnitines (in which the acyl group can be saturated $C_2$–$C_{20}$ acyl, $C_2$–$C_{20}$ acyl with 1–6 double bonds, $C_2$–$C_{20}$ hydroxyacyl with 1–3 hydroxyl groups, $C_4$–$C_{20}$ ketoacyl, unsaturated $C_5$–$C_{20}$ hydroxyacyl or $C_5$–$C_{20}$ carbalkoxyacyl) and their pharmacologically acceptable salts in combination with various classes of medicaments, such as beta-lactamase antibiotics, aminoglycosidic antibiotics, antiviral agents, amino acids, relaxing agents for the smooth musculature, polypeptides, anti-inflammatory agents and diuretics. The only example supplied in U.S. Pat. No. 4,537,772 of combination between an acyl carnitine and a medicament with cardiovascular anti-hypertensive action is a combination of palmitoyl carnitine chloride and methyl dopa. The effect foreseen in U.S. Pat. No. 4,537,772 consists of improved gastrointestinal absorption (induced by the presence of the acyl carnitine) of a medicament which is poorly absorbed when administered on its own by the oral or rectal route. It is clear that there is no correlation between the use of acyl carnitines described in U.S. Pat. No. 4,537,772 and that which forms the subject of the present invention.

Thus, there remains a need for a method to treat cardiovascular disorders. There also remains a need for pharmaceutical compositions useful for treating cardiovascular disorders.

SUMMARY OF THE INVENTION

Accordingly, it is one object of the present invention to provide a method for treating cardiovascular disorders.

It is another object of the present invention to provide a method of treating cardiovascular disorders which has a low occurrence of side effects.

It is another object of the present invention to provide novel pharmaceutical compositions for treating cardiovascular disorders.

It is another object of the present invention to provide pharmaceutical compositions which exhibit a low tendency to case side effects.

These and other objects, which will become apparent during the following detailed description, have been achieved by the inventor's discovery that the combination of (a) L-carnitine, an acyl L-carnitine, or a pharmacologically acceptable salt thereof with (b) an ACE-inhibitor offers significant advantages over previously available medicaments for treating cardiovascular disorders, such as ischemia, infarction, angina, hypertension, and congestive heart failure.

DETAILED DESCRIPTION OF THE PREFERRED EMBODIMENTS

Thus, in a first embodiment, the present invention provides pharmaceutical compositions comprising (a) L-carnitine, an acyl L-carnitine, or a pharmacologically acceptable salt thereof, and (b) an ACE-inhibitor as the active ingredients and a pharmacologically acceptable carrier or excipient. These compositions are suitable for oral, parenteral, rectal or topical (transdermal) administration.

The acyl L-carnitines useful for the pharmaceutical compositions and methods of the present invention are those wherein the acyl group is a straight or branched-chain alkanoyl group having from 2 to 8 carbon atoms, preferably from 2 to 6 carbon atoms. Particularly preferred are acetyl, propionyl, butyryl, valeryl and isovaleryl L-carnitines.

Pharmaceutically acceptable salts of L-carnitine include all pharmaceutically acceptable salts which are prepared by the addition of an acid to L-carnitine, and which do not give rise to undesired toxic or side effects. The formation of pharmaceutically acceptable acid addition salts is well known in pharmaceutical technology. Non-limiting examples of suitable salts include the chloride, bromide, orotate, acid aspartate, acid citrate, acid phosphate, fumarate, acid fumarate, lactate, maleate, acid maleate, acid oxalate, acid sulphate, glucose phosphate, tartrate and acid tartrate salts. Other suitably acceptable salts which are nontoxic and provide substantially similar results to administration of L-carnitine and the above-identified pharmaceutical salts will be readily apparent to one having ordinary skill in the art and are considered to be equivalent to the salts enumerated above.

For the sake of simplicity and clarity, hereinbelow reference will be made to L-carnitine only, it being understood, however, that whatever is disclosed in connection with L-carnitine equally applies to the above-identified acyl L-carnitine and pharmacologically acceptable salts thereof.

Suitable ACE-inhibitors include captopril, enalapril, lisinopril, ramipril, fosinopril, zofenopril, pivopril, rentiapril, quinapril, indolapril, spirapril, pentopril, benazepril, libenzapril, cilazapril, delapril and perindopril.

The compositions of the invention suitably contain from 1 to 90% by weight, preferably 25 to 75% by weight, based on the total weight of the composition, of an ACE-inhibitor and from 1 to 90% by weight, preferably 25 to 75% by weight, based on the total weight of the composition, of L-carnitine. Unit dosage forms will preferably contain from 0.5 g to 2 g of L-carnitine, while the quantity of ACE-inhibitor will depend on the characteristics of this component. For example, with specific reference to ACE-inhibitors already approved for clinical use, ramipril may be present in quantities from 1 to 10 mg, enalapril from 5 to 50 mg, captopril from 10 to 100 mg, and lisinopril from 5 to 50 mg. The composition of the present invention may also be in the form of separate dosage units for simultaneous, separate or sequential use.

In particular, compositions comprising about 1 g of L-carnitine and from 5 to 20 mg of lisinopril are preferred, for administration once per day.

Using other ACE-inhibitors having different pharmacological characteristics (such as captopril), the compositions of the invention will preferably be administered two or more times per day, up to a daily dosage of 2–3 g of L-carnitine and 20–300 mg of ACE-inhibitor.

Suitable forms of administration include capsules, tablets, syrups, granules, ampoules or phials, suppositories, or aqueous or oleous solutions. The compositions of the invention can be prepared by resorting to conventional processes and excipients, such as are described in Remington's Pharmaceutical Sciences Handbook, Mack Pub. Co., New York, USA, XVIII Ed., 1984.

In another embodiment, the present invention provides a method for treating cardiovascular disorders by administering: (a) L-carnitine, an acyl L-carnitine, or a pharmacologically acceptable salt thereof, and (b) an ACE-inhibitor to a patient in need thereof. As noted above, the cardiovascular disorders which may be treated by the present method include ischemia, infarction, angina, hypertension, and congestive heart failure.

The present method may be carried out by oral, parenteral, rectal, or transdermal administration. Oral administration is obviously preferred for chronic pathologies, while the parenteral route may be preferable for acute pathologies, for example in the case of an infarction.

Although the exact dosage ranges of (a) L-carnitine, acyl L-carnitine, or pharmacologically acceptable salt thereof and (b) the ACE-inhibitor will vary according to the exact condition being treated and the state of the patient being treated, typically, the method will comprise administering about 0.5 to 3 g, preferably about 1 to 2 g, of L-carnitine (or an equimolar amount of the acyl L-carnitine or salt thereof) daily and about 1 to 500 mg, preferably about 5 to 100 mg of the ACE-inhibitor daily. As discussed above, the dosage range of the ACE-inhibitor may be adjusted based on the exact identity of the ACE-inhibitor.

Other features of the invention will become apparent in the course of the following descriptions of exemplary embodiments which are given for illustration of the invention and are not intended to be limiting thereof.

EXAMPLES

Set out below are the results of certain clinical trials which demonstrate the advantages obtained by the present invention.

Clinical Trials 25 patients suffering from congestive heart failure as a result of coronary pathologies or of ischemia of the myocardium, who had already been treated without appreciable therapeutic response with diuretics and an ACE-inhibitor (captopril) for periods longer than 30 days, were given lisinopril (4 mg) and L-carnitine (1 g) for 15 days.

At the end of the treatment, 23 patients had a hemodynamic profile that was distinctly better, characterized by a reduction of systemic vascular resistance, an increase in contractility and cardiac output not accompanied by an increase in cardiac frequency, and a reduction in arterial pressure. Only two patients did not show significant improvements but the preliminary data indicated that extension of the period of treatment would have produced beneficial effects even in these non-responders. In none of the patients were toxic effects or side effects noted that could be attributed to the pharmacological treatment.

The results set out above show clearly that L-carnitine is able to contribute markedly to treatment with ACE-inhibitors of non-responder patients, without a need to increase the dosage.

Compositions

The following examples illustrate some typical compositions of the present invention. Example 1

| TABLETS | |
|---|---|
| Lisinopril | 5 mg |
| L-carnitine | 100 mg |
| microcrystalline cellulose | 250 mg |
| magnesium stearate | 20 mg |
| lactose | 100 mg |

Example 2

| CAPSULES | |
|---|---|
| enalapril | 10 mg |
| L-carnitine | 750 mg |
| lactose | 250 mg |

Example 3

| CAPSULES | |
|---|---|
| captopril | 50 mg |
| L-carnitine | 1000 mg |
| lactose | 500 mg |

Example 4

| TABLETS | |
|---|---|
| ramipril | 5 mg |
| L-carnitine | 350 mg |
| starch | 40 mg |
| gelatin | 10 mg |
| microcrystalline cellulose | 20 mg |
| magnesium stearate | 5 mg |

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A composition, comprising:
   (a) L-carnitine, an acyl L-carnitine (wherein the acyl group is a straight or branched alkanoyl group having 2–8 carbon atoms), or a pharmacologically acceptable salt thereof;
   (b) an ACE-inhibitor; and
   (c) a pharmacologically acceptable excipient.

2. The composition of claim 1, wherein said acyl group is an alkanoyl group having 2–6 carbon atoms.

3. The composition of claim 1, wherein said acyl group is selected from the group consisting of acetyl, propionyl, butyryl, valeryl, and isovaleryl.

4. The composition of claim 1, wherein said ACE-inhibitor is selected from the group consisting of captopril, enalapril, lisinopril, ramipril, fosinopril, zofenopril, pivopril, rentiapril, quinapril, indolapril, spirapril, pentopril, benazepril, libenzapril, cilazapril, delapril, and perindopril.

5. The composition of claim 1, which in unit dosage form comprises: (a) from 0.5 to 2 g of L-carnitine or an equimolar amount of said acyl L-carnitine or said pharmacologically acceptable salt thereof; and (b) from 1 to 50 mg of said ACE-inhibitor.

6. The composition of claim 1, which is in a form suitable for oral, parenteral, rectal, or transdermal administration.

7. A method of treating a patient suffering from a cardiovascular disorder, comprising administering an effective amount of:
   (a) L-carnitine, an acyl L-carnitine (wherein the acyl group is a straight or branched alkanoyl group having 2–8 carbon atoms), or a pharmacologically acceptable salt thereof; and
   (b) an ACE-inhibitor, to said patient.

8. The method of claim 7, wherein said acyl group is an alkanoyl group having 2–6 carbon atoms.

9. The method of claim 7, wherein said acyl group is selected from the group consisting of acetyl, propionyl, butyryl, valeryl, and isovaleryl.

10. The method of claim 7, wherein said ACE-inhibitor is selected from the group consisting of captopril, enalapril, lisinopril, ramipril, fosinopril, zofenopril, pivopril, rentiapril, quinapril, indolapril, spirapril, pentopril, benazepril, libenzapril, cilazapril, delapril, and perindopril.

11. The method of claim 7, comprising administering a unit dosage which comprises: (a) from 0.5 to 2 g of L-carnitine or an equimolar amount of said acyl L-carnitine or said pharmacologically acceptable salt thereof; and (b) from 1 to 50 mg of said ACE-inhibitor.

12. The method of claim 7, wherein said administering is carried out by oral, parenteral, rectal, or transdermal administration.

13. The method of claim 7, wherein said cardiovascular disorder is selected from the group consisting of ischemia, infarction, angina, hypertension, and congestive heart failure.

14. The method of claim 7, wherein said cardiovascular disorder is myocardial ischemia.

15. The composition as claimed in claim 1, wherein said composition is in a form selected from the group consisting of capsules, tablets, syrups, granules, ampoules, phials, suppositories, aqueous solutions and oleous solutions.

16. The method as claimed in claim 7, wherein said treatment is effected by administration of said effective amount of (a) and (b) in a form selected from the group consisting of capsules, tablets, syrups, granules, ampoules, phials, suppositories, aqueous solutions and oleous solutions.

17. The method as claimed in claim 7, wherein said effective amount of (a) and (b) is a daily dosage of from 1 to 3 g per day of (a) and from 5 to 300 mg of (b).

* * * * *

UNITED STATES PATENT AND TRADEMARK OFFICE
CERTIFICATE OF CORRECTION

PATENT NO. : 5,861,434
DATED : January 19, 1999
INVENTOR(S) : Claudio CAVAZZA

It is certified that error appears in the above-identified patent and that said Letters Patent is hereby corrected as shown below:

On the title page, item [30], Foreign Application Priority Data is missing. It should be:

--[30]  Foreign Application Priority Data
Mar. 27, 1992 [IT] Italy ............. RM 92 A 000222--

Signed and Sealed this

Sixth Day of July, 1999

Attest:

Q. TODD DICKINSON

Attesting Officer

Acting Commissioner of Patents and Trademarks